United States Patent [19]

Leonidov

[11] Patent Number: 5,602,281
[45] Date of Patent: Feb. 11, 1997

[54] PROCESS FOR PREPARING PHYSICALLY STABLE CRYSTALLINE GAMMA MODIFICATION OF PARA-AMINOBENZENESULFONAMIDE

[76] Inventor: Nikolai B. Leonidov, ulitsa Zatonnaya, Korpus 1, kv. 158, Moscow, Russian Federation

[21] Appl. No.: 416,830
[22] PCT Filed: Nov. 16, 1993
[86] PCT No.: PCT/RU93/00274
  § 371 Date: May 11, 1995
  § 102(e) Date: May 11, 1995
[87] PCT Pub. No.: WO95/05361
  PCT Pub. Date: Feb. 23, 1995

[30] Foreign Application Priority Data

Aug. 19, 1993 [RU] Russian Federation ............ 93041684

[51] Int. Cl.$^6$ ..................... C07C 311/39; C07C 303/44
[52] U.S. Cl. ............................................. 564/86
[58] Field of Search ................................. 564/86

[56] References Cited

FOREIGN PATENT DOCUMENTS

| | | |
|---|---|---|
| 704447 | 2/1941 | Germany . |
| 136363 | 5/1961 | U.S.S.R. . |
| 433672 | 6/1974 | U.S.S.R. . |
| 513242 | 10/1939 | United Kingdom . |

OTHER PUBLICATIONS

Lin, H. O. et al. "Polymorphism in Sulfanilamide-d4" Journal of Pharmaceutical Sciences 59(7), 972–975 (1970).

The Merck Index; Eleventh Edition; Merck & Co.:Rahway, NJ, 1989; pp. 1408–1409.

A. Watanabe and E. Kamio, *J. Pharm. Soc. Japan*, vol. 63, No. 11 (1942): 17–19.

*Primary Examiner*—Johann Richter
*Assistant Examiner*—Michael G. Ambrose
*Attorney, Agent, or Firm*—Ladas & Parry

[57] ABSTRACT

A process for preparing a physically stable crystalline γ-modification of para-aminobenzenesulfonamide comprises cooling a para-aminobenzenesulfonamide solution in water or an organic solvent at rate of at least 2° C./min to complete crystallization thereof and subsequently separating the resulting crystals and drying thereof.

12 Claims, No Drawings

PROCESS FOR PREPARING PHYSICALLY STABLE CRYSTALLINE GAMMA MODIFICATION OF PARA-AMINOBENZENESULFONAMIDE

This is a U.S. national stage application under 35 U.S.C. §371 based upon PCT International Application No. PCT/RU93/0024, filed on Nov. 16, 1993.

FIELD OF ENGINEERING

The present invention relates to organic chemistry, more particularly to a process for preparing a physically stable crystalline γ-modification of para-aminobenzenesulfonamide.

PRIOR ART

It is well known that para-aminobenzenesulfonamide may crystalline at least in three polymorphous modifications designed as α-, β- and γforms (Journal of Pharmaceutical Sciences, v. 59, No. 7, July 1970, p. 972–975; Journal of Pharmaceutical of Japan, 1942, v. 63, No. 11, p. 17–19) from which only the α-form is being used in medical practice. Said polymorphous modifications can be prepared by crystallization and conversion of one form into the other.

The crystalline γ-modification of para-aminobenzenesulfonamide can be prepared by dissolving in amyl alcohol of β-modification followed by boiling. The resulting crystals are thermally insulated, gradually cooled to room temperature and filtered. The γ-modification is identified by a radiographic analysis method.

Also known in the art is a process for preparing the γ-modification of para-aminobenzenesulfonamide by pulverization of α- and β-modifications and subsequently heating the resulting powder at 130°–140° C. for 1 hour. In this case, the β-modification is converted into the γ-modification. However, the γ-modification of para-aminobenzenesulfonamide prepared by the processes indicted above is unstable at room temperature and is converted into the β-modification which is then spontaneously converted into the γ-modification. Since the resulting γ-modification is unstable, its pharmacological activity has not been investigated. Said processes for preparing the γ-modification of para-aminobenzenesulfonamide have not been used on an industrial scale.

DISCLOSURE

The object of the invention is to provide a process by changing the technological operations which would make it possible to obtain a physically stable crystalline γ-modification of para-aminobenzenesulfonamide having high antimicrobial and interferon-inducing The problem can be solved in that in the claimed process for preparing a physically stable crystalline γ-modification of para-aminobenzenesulfonamide having, a solution of para-aminobenzenesulfonamide in water or an organic solvent or in a mixture thereof is cooled with a cooling agent at a rate of not lower than 2° C./min to complete crystallization thereof followed by separation of resulting crystals and drying thereof.

It is desirable to use lower alcohols, preferably ethanol, as organic solvent. To increase the yield of the desired product, it is desirable to use liquid nitrogen or liquid carbon dioxide as the cooling agent, and to carry out the drying operation by vaccum treatment at a pressure not higher than $10^{-2}$ mm Hg.

The claimed process makes it possible to obtain a physically stable crystalline γ-modification of para-aminobenzenesulfonamide which is stable during storage at room temperature and has antimicrobial activity higher than the activity of the β- and α-forms used in medical practice and also has a highly effective interferon-inducing activity. The claimed process is characterized by simply technology and suitable for industrial use.

BETTER EMBODIMENT OF THE INVENTION

The claimed process for preparing a physically stable crystalline γ-modification of para-aminobenzenesulfonamide is carried out by cooling a solution of para-aminobenzenesulfonamide in water or an organic solvent or in a mixture thereof with a cooling agent at a rate of at least 2° C./min to complete crystallization thereof followed by separation of the resulting crystals and drying thereof. The cooling agent may be any substance capable of reducing the temperature of the substance to be cooled at a rate of at least 2° C./min. The optical substance used as the cooling agent is liquid nitrogen or liquid carbon dioxide, the use of these substances increases the yield of the desired product by quickly establishing and further maintaining the required cooling rate.

A physically stable crystalline γ-modification of said compound can be prepared at a cooling rate of least 2° C./min. The process carried out at a cooling rate of lower than 2° C./min does not make it possible to obtain new crystalline modification. The upper cooling rate is not restricted. At any maxim highest attainable cooling rate of the starting solution, a new crystalline modification is formed. The cooling process is carried out in water or in any organic solvent or in a mixture thereof in which the starting substance is soluble. Preferred solvents are water and lower alcohols, preferably ethanol. In this case, the highest yield of the desired product attained. The claimed substance can be obtained irrespective of the concentration of the starting substance in solution. The drying conditions at pressure higher $10^{-2}$ mm Hg are chosen because the final dried product should have a moisture content of not higher than 3%. The resulting desired product is a physically stable crystalline γ-modification of para-aminobenzenesulfonamide represents a white fine powder (crystals of elbow form typical of the γ-modification). The analysis of the spectra and X-ray diagrams confirms the fact that the resulting desired product is γ-modification of said compound and is defined by the following values of interplane distances d and reflex relative intensities I:

| d, Å | I |
| --- | --- |
| 7.63 | 31 |
| 6.61 | 73 |
| 6.28 | 8 |
| 6.00 | 3 |
| 5.64 | 30 |
| 4.90 | 71 |
| 4.51 | 100 |
| 4.27 | 4 |
| 4.19 | 5 |
| 3.80 | 98 |
| 3.66 | 30 |
| 3.56 | 32 |
| 3.47 | 4 |
| 3.36 | 4 |
| 3.23 | 8 |
| 3.20 | 12 |
| 3.13 | 13 |

-continued

| d, A  | I  |
|-------|----|
| 3.04  | 30 |
| 2.99  | 25 |
| 2.81  | 13 |
| 2.67  | 2  |
| 2.64  | 3  |
| 2.62  | 2  |
| 2.53  | 5  |
| 2.49  | 10 |
| 2.46  | 6  |
| 2.33  | 9  |
| 2.25  | 6  |
| 2.22  | 4  |
| 2.21  | 4  |
| 2.17  | 4  |
| 2.16  | 4  |
| 2.14  | 4  |
| 2.12  | 8  |
| 2.11  | 9  |
| 1.99  | 5  |
| 1.97  | 6  |

-continued

| d, A  | I  |
|-------|----|
| 1.93  | 4  |
| 1.92  | 5  |
| 1.91  | 5  |
| 1.88  | 5  |
| 1.86  | 4  |
| 1.84  | 3  |
| 1.82  | 4  |
| 1.80  | 5  |
| 1.77  | 3  |
| 1.75  | 3  |
| 1.727 | 5  |
| 1.618 | 4  |
| 1.583 | 3  |
| 1.566 | 4  |

The resulting physically stable crystalline γ-modification of para-aminobenzenesulfonamide has an antimicrobial and interferon-inducing activity.

The activity of the resulting γ-modification was investigated in experiments on animals as compared with pharmacopean para-aminobenzenesulfonamide (comprising substantially the α-modification) used in medical practice.

In order to investigate the specific antimicrobial activity, a method of serial dilutions was used. The starting solutions were 0.5% solutions of pharmacopean para-aminobenzenesulfonamide and the γ-modification of said compound in a 0.1 N sodium hydroxide solution.

Two-fold dilutions of the test solutions were prepared in a meat peptonic broth with the addition of Staphylococcus aureas. The seeds were kept in a thermostat for 24 hours. The bacteriostatic concentration was determined visually. Sterile and non-sterile solutions of para-aminobenzenesulfonamide and of the γ-modification were used.

The experiments were carried out in three series of the test solutions on three-fold dilutions.

The results are presented in Table 1. The analysis of the data presented in Table 1 is indicative of the fact that the γ-modification has antimicrobial activity which is not inferior to the activity of the pharmacopean para-aminobenzenesulfonamide.

TABLE 1

| Nos 1 | Test agent 2 | 0 3 | 1 4 | 2 5 | 3 6 | Control 7 |
|-------|--------------|-----|-----|-----|-----|-----------|
| 1 | Sterile solvent | No growth | Growth | Growth | Growth | Growth |
| 2 | Pharmacopean para-aminobenzenesulfonamide | No growth | No growth | No growth | Growth | Growth |
| 3 | γ-modification of para-aminobenzenesulfonamide | No growth | No growth | No growth | Growth | Growth |
| 4 | Non-sterile solvent | No Growth | Growth | Growth | Growth | Growth |
| 5 | Pharmacopean para-aminobenzenesulfonamide (non-sterile agent) | No growth | No growth | No growth | Growth | Growth |
| 6 | γ-modification of para-aminobenzenesulfonamide (non-sterile agent) | No growth | No growth | No growth | Growth | Growth |

The investigation of the toxic effects of the γ-modification of para-aminobenzensulfonamide as compared with pharmacopean para-aminobenzenesulfonamide showed that the γ-modification has lower toxicity, namely, $LD_{50}$ is 1918 m%/kg of animal body when administered intraperitoneally, whereas $LD_{50}$ of the pharmacopean agent is 1242 mg/kg of animal body. The interferon-inducing activity of he γ-modification of para-aminobenzenesulfonamide was compared with that of pharmacopean para-aminobenzenesulfonamide on mice in vivo experiments.

The experiments used CBA strain male rats weighing 10–12 g and Z-929 mouse fibro-blast intertwine cell strain. The cells were grown in plastic 96-hole plates (37° C., 3.5% CO) in medium Needle 2 HEM of 10% cattle serum. The mouse encephalocardite virus (the Columbia strain) was chosen as a virus.

The pharmacopean agent and the γ-modification of para-aminobenzenesulfonamide were administered singly intraperitoneally (0.2 ml per mouse) at 50 and 150 mkg/0.2 ml doses. The blood was taken from the carotid 5, 24 and 72 hours after administration of the agents. At least 5 animals were used for each sample. The interferon titration was carried out by determining the suppression of a cytopathic effect on the cell culture by using a micromethod.

The investigation results are presented in Table 2.

TABLE 2

Dynamics of Interferon Formation of the Mouse
Blood Serum during Administration of Test Agents

| Nos | Agent | Blood/time after administration of agent, Hr | Interferon titers (units/ml) Agent concentration, 50 mkg/mouse | Interferon titers (units/ml) Agent concentration, 150 mkg/mouse |
|---|---|---|---|---|
| 1 | 2 | 3 | 4 | 5 |
| 1 | Pharmacopean para-aminobenzenesulfonamide | 5 | <20 | <20 |
|   |   | 24 | <20 | <20 |
|   |   | 72 | <20 | <20 |
| 2 | γ-modification of para-aminobenzenesulfonamide | 5 | 40–80 | 80 |
|   |   | 24 | 160 | 320 |
|   |   | 72 | <20 | <20 |
| 3 | Control | 5 |  | <20 |
|   |   | 24 |  | <20 |
|   |   | 72 |  | <20 |
| 4 | Mouse serum interferon | — |  | 640 |

The analysis of the investigation results showed that pharmacopean para-aminobenzenesulfonamide has no interferon-inducing activity. At the same time the γ-modification of this agent induced interferon in the mouse blood serum as early a 5 hours after administration (early interferon) with an activity of 40–80 units/ml, and after 24 hours the interferon titers were as high as 160–320 units/ml. By the end of 72 hours the interferon titers became lower. Thus the crystalline γ-modification of para-aminobenzenesulfonamide obtained by the claimed process is physically stable form having a highly effective antimicrobial and interferon-inducing activity. In order to better understand the present invention, the following examples are provided on the preparation of a physically stable crystalline γ-modification of para-aminobenzenesulfonamide.

EXAMPLE 1

1.5 l of an aqueous solution of para-aminobenzenesulfonamide having a concentration of 20 g/l are cooled with liquid nitrogen at a cooling rate of 2° C./min to complete crystallization thereof. The resulting frozen mass is transferred to trays and placed into subliminator. The drying operation is carried out at a pressure of $10^{-2}$ mm Hg to a residual moisture content of 3%. The yield of the desired product is 30%( 100%). The resulting product is a white fine crystalline powder. The resulting substance is characterized by the values of interplanar distances d and relative reflexes I identical with the corresponding values of the crystslline γ-modification of para-aminobenzenesulfonamide given above.

EXAMPLE 2

The process is carried out as described in Example 1. In this case, 500 ml of a solution of the starting agent are used in a water/ethanol (1:1 ) mixture having a concentration of 20 g/l . The yield of the desired product is 96 wt %. The resulting agent ha characteristics similar to those described in Example 1.

EXAMPLE 3

The process is carried out as described in Example 1 at a cooling rate of 30° C./min. The yield of the desired product is 98.2 wt %. The resulting product has characteristics similar to those in Example 1.

EXAMPLE 4

1.5 l of a para-aminobenzenesulfonamide solution in ethanol having a concentration of 10 g/l are cooled with liquid nitrogen at a cooling rate of 8° C./min to complete crystallization of the solution. The resulting frozen mass is placed into a sublimator. The drying operation is carried out at a pressure of $10^{-2}$ mm Hg. The yield of the desired product is 95.6 wt %. The resulting compound has characteristics similar to those in Example 1.

EXAMPLE 5

The process is carried out as described in Example 1. The concentration of the starling compound in ethanol 10 g/l, and the cooling agent is liquid carbon didoxide.

The yield of the desired product is 96.8 wt %. The resulting compound has characteristics similar to those in Example 1.

INDUSTRIAL APPLICABILITY

The physically stable crystalline γ-modification obtained by the claimed process has highly effective antimicrobial and interferon-inducing activity and find applications in medical practice as the active ingredient of the drug.

I claim:

1. A process for preparing a physically stable crystalline gamma modification of para-aminobenzenesulfonamide, the process comprising the steps of:
    (a) providing a solution of para-aminobenzenesulfonamide in water, in an organic solvent, or in a mixture of water and organic solvent;
    (b) cooling the solution with a cooling agent at a rate of at least 2° C./min to form crystals of the gamma modification of para-aminobenzenesulfonamide; and
    (c) separating and drying the crystals formed in step (b).

2. A process according to claim 1, wherein the organic solvent comprises a lower alcohol.

3. A process according to claim 2, wherein the lower alcohol is ethanol.

4. A process according to claim 1, wherein the cooling agent is liquid nitrogen or liquid carbon dioxide, and the drying is carried out by vacuum treatment at a pressure not higher than $10^{-2}$ mm Hg.

5. A process according to claim 2, wherein the cooling agent is liquid nitrogen or liquid carbon dioxide, and the drying is carried out by vacuum treatment at a pressure not higher than $10^{-2}$ mm Hg.

6. A physically stable crystalline gamma modification of para-aminobenzenesulfonamide prepared by a process comprising:
    a) cooling using a cooling agent a solution of para-aminobenzenesulfonamide at a rate of at least 2° C./min to form crystals of the gamma modification of para-aminobenzenesulfonamide; and
    b) separating and drying the crystals formed in step a).

7. The physically stable crystalline modification of para-aminobenzenesulfonamide prepared according to claim 6, wherein the para-aminobenzenesulfonamide solution is para-aminobenzenesulfonamide in water, an organic solvent or a mixture thereof.

8. The physically stable crystalline modification of para-aminobenzenesulfonamide prepared according to claim 7, wherein the organic solvent is a lower alcohol.

9. The physically stable crystalline modification of para-aminobenzenesulfonamide prepared according to claim 7, wherein the organic solvent is ethanol.

10. The physically stable crystalline modification of para-aminobenzenesulfonamide prepared according to claim 6, wherein the cooling agent is liquid nitrogen or liquid carbon dioxide.

11. The physically stable crystalline modification of para-aminobenzenesulfonamide prepared according to claim 6, wherein the drying is carried out by vacuum treatment at a pressure not higher than $10^{-2}$ mm Hg.

12. A process according to claim 3, wherein the cooling agent is liquid nitrogen or liquid carbon dioxide, and the drying is carried out by vacuum treatment at a pressure not higher than $10^{-2}$ mm Hg.

* * * * *